United States Patent [19]
Schrenk et al.

[11] Patent Number: 5,316,731
[45] Date of Patent: May 31, 1994

[54] DEVICE FOR COLLECTION AND PROCESSING OF BIOLOGICAL SAMPLES

[75] Inventors: W. Juergen Schrenk, Cranbury; Shelby J. Hall, Hamilton, both of N.J.

[73] Assignee: Carter-Wallace, Inc., New York, N.Y.

[21] Appl. No.: 973,734

[22] Filed: Nov. 9, 1992

[51] Int. Cl.$^5$ ............................ B01L 3/00; B03B 5/00
[52] U.S. Cl. ............................ 422/101; 210/322.85; 210/433.1
[58] Field of Search ................. 422/101; 435/311; 210/321.85, 433.1

[56] References Cited

U.S. PATENT DOCUMENTS 4,966,758 10/1990 Belt ....................................... 422/101
4,995,967 2/1991 van Driessche ................. 435/311 X Primary Examiner—Jill A. Johnston
Attorney, Agent, or Firm—Elliot M. Olstein; Raymond J. Lillie

[57] ABSTRACT

A sample collection container having inner and outer chambers. The container may be fitted with upper and lower stoppers to provide a vacuum within the container. The device is adapted for the collection of a fluid, such as blood, in the inner chamber. The blood then passes from the inner chamber to the outer chamber upon releasing the vacuum. A concentrate of fluid components of blood, cellular debris, and contaminating microorganisms, if present, may be left in the inner chamber, and be removed subsequently from the inner chamber for testing for the presence of contaminating microorganisms.

10 Claims, 2 Drawing Sheets

DEVICE FOR COLLECTION AND PROCESSING OF BIOLOGICAL SAMPLES

This invention relates to devices and methods for collecting and processing of biological samples, such as, for example, blood and serum samples. More particularly, this invention relates to an apparatus for the collection and processing of biological samples which does not require centrifugation of the sample.

Biological samples, such as blood and serum samples, for example, are often tested for microbial infections. In general, blood may be collected in a sample tube which contains a reagent which causes lysis of red and white blood cells, but not of microbial contaminants. The tube is then placed in a centrifuge. Centrifugation results in the separation of the sample into a supernatant and a concentrate which contains cellular debris and microbial contaminants, if present. The supernatant is removed from the sample, and the remaining concentrate is then tested for the presence of microbial contaminants, generally by streaking such concentrate onto a culture plate, and incubating the culture.

Such processing procedures, however, require an appreciable amount of equipment and expense, as well as a considerable amount of time. The collection and processing of a blood sample for testing for microbial contamination may require a period of time of up to 45 minutes.

It is therefore an object of the present invention to provide an apparatus for the collection and processing of blood for further testing without the time and expense involved in centrifugation.

In accordance with an aspect of the present invention, there is provided a container which comprises a first chamber and a second chamber. The container is under vacuum. The container also includes a first means for selectively placing the first chamber in fluid flow communication with the second chamber, and a second means for introducing material into the first chamber without releasing the vacuum of the second chamber. The container further includes a retaining means in the first chamber for retaining the solid component of a mixture of solids and liquid which is introduced into the first chamber, and means for selectively placing the interior of the container in communication with the atmosphere outside the container. After introduction of a mixture into the container, liquid passes through the retaining means and through the first means for selectively placing the first chamber in fluid flow communication with the second chamber with the solid component being retained on the retaining means.

In a preferred embodiment, the second chamber surrounds the first chamber and is concentric with the first chamber. The first chamber is defined by an inner wall, and the second chamber is defined by the inner wall and an outer wall. The inner wall protrudes above the top of the second chamber.

In one embodiment, the first means for selectively placing the first chamber in fluid flow communication with the second chamber comprises a lower stopper fitting within a bottom opening of the container. The stopper includes a lower passage communicating with the first chamber, and a passage in the inner wall adjacent the second chamber. The lower passage of the lower stopper is capable of being aligned with the passage of the inner wall adjacent the second chamber to provide for the flow of liquid from the first chamber to the second chamber.

In one preferred embodiment, the retaining means includes a membrane, which is disposed across the lower passage of the lower stopper which communicates with the first chamber. More preferably, the lower stopper includes a lower portion and an upper insert portion which includes the passage communicating with the first chamber. In one alternative embodiment, the passage has a inverted conical shape, whereby the liquid is funneled from the inner chamber toward the second, or outer chamber. The upper insert portion also includes the membrane disposed across the lower passage communicating with the first chamber.

In another embodiment, the means for selectively placing the interior of the container in communication with the atmosphere outside the container includes an upper stopper fitting within a top opening of the container. The upper stopper includes an upper passage communicating with the first chamber. The means for selectively placing the interior of the container in communication with the outside atmosphere also includes an opening in the inner wall above the top of the second chamber. The upper passage of the upper stopper is capable of being aligned with the opening in the inner wall to release the vacuum and provide for the passage of air from the outside atmosphere into the container. Preferably, the upper stopper also includes the second means for introducing material into the first chamber.

In a preferred embodiment, the upper stopper includes an upper portion and a lower portion. The lower portion fits within the top opening of the container. The lower portion includes the upper passage communicating with the first chamber. The second means for introducing material into the first chamber without releasing the vacuum of the second chamber is a first self-sealing portion included in the upper portion of the stopper, and a second self-sealing portion included in the lower portion of the stopper. In one embodiment, the second self-sealing portion is a one-way valve fitting within the first chamber.

In another embodiment, an airtight layer is placed between the upper and lower portions of the upper stopper. The airtight layer may be, for example, a laminated foil which is laminated to the underside of the upper portion of the upper stopper. In another embodiment, the lower portion of the upper stopper also has an airtight layer laminated to its bottom. In yet another embodiment, a thick rubber wall is attached to the underside of the upper portion of the stopper.

In another alternative, a sterile filter layer is placed between the upper and lower portions of the upper stopper.

In yet another alternative, a sterile filter plug is contained within the lower portion of the upper stopper. The sterile filter plug is made of a porous material such as, for example, cotton, foam rubber, sintered polyethylene, aluminum oxide, sintered glass, or fiberglass. The porosity of the sterile filter plug should be such that the filter plug allows the passage of air through the filter plug yet is able to trap contaminants such as microorganisms within the filter plug. The filter plug also permits the insertion of a conduit, such as an injection needle, through the filter plug, and the withdrawal of such a conduit from the filter plug while maintaining the structural integrity of the filter plug. In such an embodiment, the upper portion of the upper stopper is removable from the lower portion. When the upper portion of the upper stopper is removed from the lower portion, the lower portion of the upper stopper and the sterile filter plug contained within the lower portion are exposed to the surrounding atmosphere. Air passes through the filter plug contained in the lower portion of the upper stopper and into the inner chamber. Such an embodiment, therefore, does not require alignable openings in the upper stopper and in the wall of the upper chamber.

The container of the present invention is particularly applicable to the collection and processing of blood samples for testing for microbial contamination. A blood sample may be introduced into the first, or inner chamber via a syringe needle inserted through the self-sealing portion(s) of the upper stopper. The upper and lower stoppers are in the closed position. Contained in the inner chamber is a reagent which lyses red and white blood cells but not microbial contaminants. An example of such a reagent is the Isolator TM 10 reagent (Carter-Wallace, Inc.), which contains saponin, polypropylene glycol, sodium polyanethole sulfonate (SPS), and ethylenediamine tetraacetic acid (EDTA). Once the blood has reacted with the reagent, the upper and lower stoppers are moved to the open position. When the stoppers are moved to the open position, air is drawn through the opening in the wall of the first, or inner chamber above the top of the outer chamber, through the upper passage of the upper stopper, and into the inner chamber. The air pressure forces the blood through the membrane of the lower stopper, through the lower passage of the lower stopper, and through the opening of the wall of the inner chamber which is adjacent the second, or outer chamber, whereby blood flows into the outer chamber. Alternatively, when an upper stopper which includes a filter plug contained in the lower portion is employed, the removal of the upper portion of the upper stopper from the lower portion of the upper stopper enables air to pass through the filter plug and into the inner chamber, whereby the passage of air into the inner chamber enables blood to flow from the inner chamber to the outer chamber. Cellular debris and contaminating microorganisms, if present, are trapped by the membrane. A small portion of the blood remains in the inner chamber. A pipette may then be inserted through the upper stopper to remove the blood, cellular debris, and microorganisms, if present, from the inner chamber. This blood sample, which is analogous to a concentrate obtained in a centrifugation procedure, may then be subjected to testing for microbial contamination.

The invention will now be described with respect to the drawings, wherein.

Figure 1:
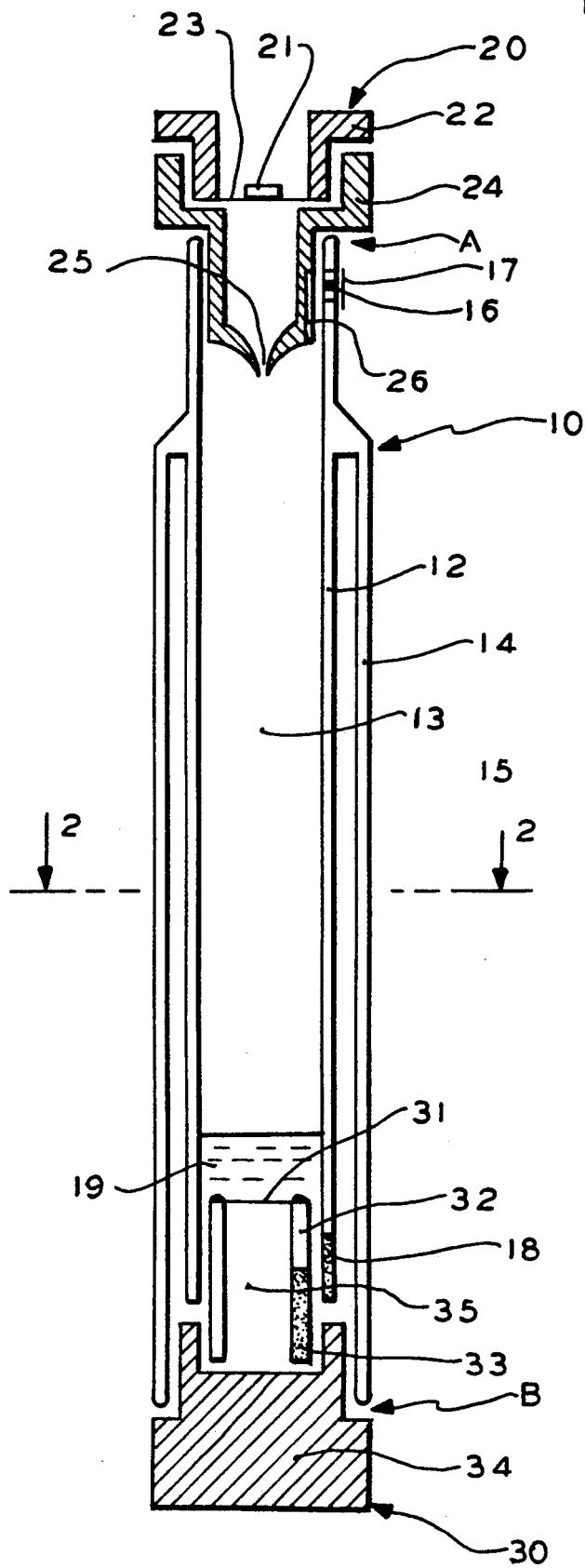
FIG. 1 is a cross-sectional view of an embodiment of the container of the present invention.
Figure 2:
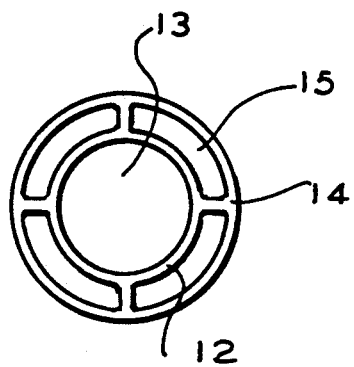
FIG. 2 is a cross-sectional view of the container.

Referring now to the drawings, the container 10 includes a top opening A and a bottom opening B. Container 10 includes an inner wall 12 and an outer wall 14, which define a first, or inner chamber 13 and a second, or outer chamber 15. Inner wall 12 and outer wall 14 merge at the top of outer chamber 15, thereby sealing outer chamber 15 at its top end. Inner wall 12 protrudes above the top of outer chamber 15. An opening 16, covered by a 0.2 μ membrane 17 is located in inner wall 12 above the top of outer chamber 15. Membrane 17 allows the passage of air through opening 16, but prevents the passage of particles and contaminating microorganisms. A passage 18 is located on inner wall 12 adjacent outer chamber 15. Passage 18, which may be in the form of an opening or a notch, provides for the passage of air or liquid between inner chamber 13 and outer chamber 15.

Fitting within the top opening A of container 10 is upper stopper 20. Upper stopper 20 includes an upper portion 22 and a lower portion 24. Upper portion 22 includes a self-sealing center 21, made of a self-sealing material such as rubber, and an airtight layer 23 on the underside of upper portion 22. The airtight layer may be made of any of a variety of materials, such as foil. The lower portion 24 includes a self-sealing one-way valve 25, and an opening 26. Opening 26 may be aligned with opening 16 in inner wall 12 to provide for the passage of air through lower portion 24 of upper stopper 20, and into inner chamber 13.

Fitting within bottom opening B of container 10 is bottom stopper 30. Bottom stopper 30 includes an upper insert portion 32 which fits within lower portion 34. Disposed at the top of upper insert portion 32 is a 0.2 μ membrane 31. Membrane 31 allows the passage of liquid components of blood into passage 35, but prevents the passage of cellular debris and microorganisms. Upper insert portion 32 also includes an opening 33. Opening 33 may be aligned with passage 18, thereby allowing the fluid portion of blood to pass from inner chamber 13 through membrane 31, passage 35, opening 33, and passage 18 into outer chamber 15.

The container 10 is employed for the collection of blood as follows. Upper stopper 20 is positioned within top opening A of container 10 such that opening 26 is not aligned with opening 16 of inner wall 12. Lower stopper 30 is positioned within bottom opening B of container 10 such that opening 33 is not aligned with passage 18 of inner wall 12. Such positioning of the upper and lower stoppers 20 and 30, respectively, preserves the vacuum within inner chamber 13 and outer chamber 15 of container 10, which was created during the manufacturing and assembly of the device. A reagent 19 which causes lysis of red and white blood cells is contained within inner chamber 13. Reagent 19 settles on top of membrane 31 within inner chamber 13 due to gravity. For specimen collection, a specimen, such as a blood sample, is injected into inner chamber 13 by means of an injection needle inserted through self-sealing centers 21 and 25. The blood is admixed with reagent 19 in inner chamber 13, and the blood is reacted with reagent 19 for a period of time sufficient to cause lysis of red and white blood cells. Such reaction time may be from about 1 minute to about 5 hours. Reagent 19, however, will not cause lysis of contaminating microorganisms.

Upon reaction of the blood with reagent 19 to cause lysis of red and white blood cells, upper stopper 20 is turned within top opening A such that opening 26 is aligned with opening 16, and bottom stopper 30 is turned such that opening 33 is aligned with passage 18. Air pressure caused by air passing through membrane 17, and openings 16 and 26 into inner chamber 13 enables the fluid portion of the blood to pass through membrane 31, passage 35, opening 33, and passage 18 into outer chamber 15. The container 10 is operated such that a portion of the blood will remain in inner chamber 13. If the volume of blood placed in inner chamber 13 is greater than the total volume of outer chamber 15, the blood will flow from inner chamber 13 to outer chamber 15 until outer chamber 15 is filled. If the total volume of outer chamber 15 is greater than the volume of blood placed in inner chamber 13, the blood is allowed to flow from inner chamber 13 to outer chamber 15 until a specified volume of blood remains in inner chamber 13. When the specified volume of blood is remaining in inner chamber 13, the indication of such volume being shown in the form of markings (not shown) on container 10, the bottom stopper 30 is turned from the open position to a closed position in which opening 33 is not aligned with passage 18.

The portion of the blood sample which remains in inner chamber 13 is a concentrate of fluid components of blood, cellular debris, and microorganisms, if present. This concentrate may then be withdrawn from the inner chamber 13. Prior to withdrawal of the concentrate, the tube is vortexed briefly (e.g., about 10 seconds). The upper portion 22 of upper stopper 20 is removed from lower portion 24 to expose the self-sealing center 25. A collection tube, such as a pipette, is inserted through center 25, and into inner chamber 13. The pipette is inserted into inner chamber 13 to a point just above membrane 31. The concentrate is then withdrawn from inner chamber 13 into the pipette, from which the concentrate may be dispensed onto a culture medium to determine the presence of contaminating microorganisms.

Figure 3:
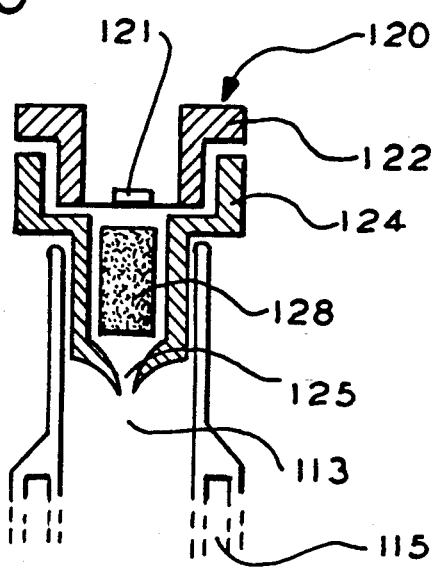
FIG. 3 is a cross-sectional view of an alternative embodiment of the upper stopper of the container.

In one alternative, as shown in FIG. 3, there is provided an upper stopper 120 having an upper portion 122, and lower portion 124. Upper portion 122 includes a self-sealing center 121. Lower portion 124, which fits within inner chamber 113, includes one-way valve 125, which prevents backflow of fluid in inner chamber 113. Contained within lower portion 124 is a sterile filter plug 128. Filter plug 128 is made of a porous material such as cotton or foam rubber. When upper portion 122 of upper stopper 120 is removed from lower portion 124, air passes through filter plug 128 through one-way valve 125; and into inner chamber 113; whereby the blood sample contained in inner chamber 113 may pass to outer chamber 115. Filter plug 128 also entraps contaminants contained in the air, such as microorganisms. Subsequent to the passage of the blood sample from inner chamber 113 to outer chamber 115, the filter plug 128 may be removed from the lower portion 124 so as to accommodate the insertion of a pipette or other collection tube through lower portion 124 for withdrawal of a concentrate from inner chamber 113.

Figure 4:
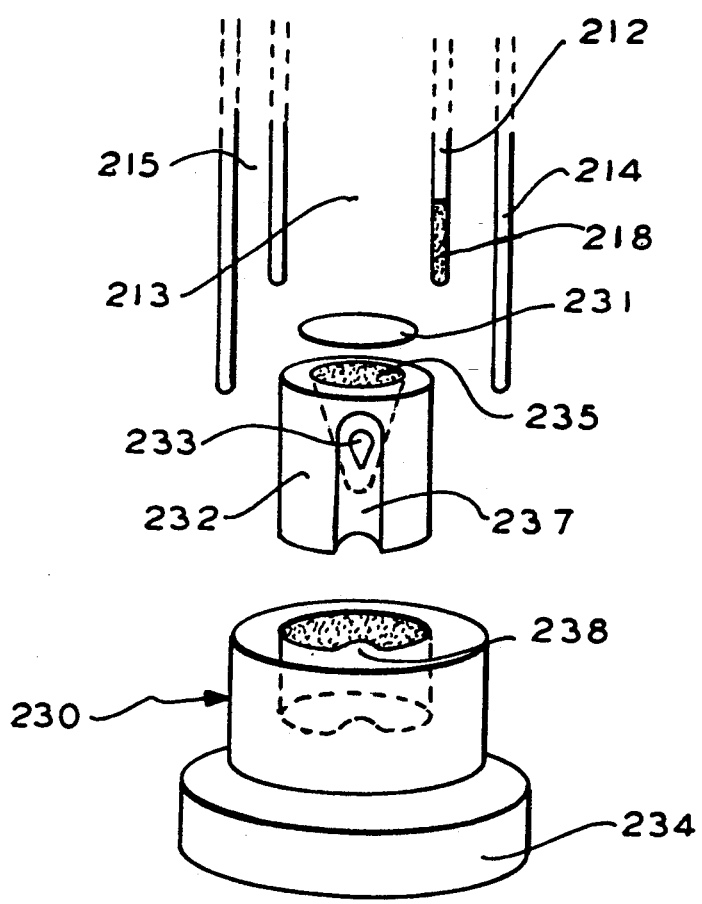
FIG. 4 is an exploded view of an alternative embodiment of the lower stopper of the container.

In another alternative, as shown in FIG. 4, lower stopper 230 is provided with an upper insert portion 232 and a lower portion 234. Upper insert portion 232, which fits within inner chamber 213 and into lower portion 234, includes a membrane 231 disposed above an inverted conical passage 235. Near the apex of conical passage 235 is an opening 233, which may be aligned with passage 218 in inner wall 212, thereby allowing the passage of the fluid components of blood from inner chamber 213 to outer chamber 215. Upper insert portion 232 also includes a groove 237, which mates with notch 238 of lower portion 234 to provide a secure fitting of upper insert portion 232 within lower portion 234.

Advantages of the present invention include the ability to provide a concentrate of a fluid portion of blood which contains cellular debris and contaminating microorganisms, if present, without subjecting a blood sample to time-consuming and expensive centrifugation techniques. The collection and processing of a blood sample with the device of the present invention may be accomplished in about 5 minutes, whereas collecting and processing of a blood sample using conventional centrifugation techniques may take 45 minutes or more.

It is to be understood, however, that the scope of the present invention is not to be limited to the specific embodiments described above. The invention may be practiced other than as particularly described and still be within the scope of the accompanying claims.

What is claimed is:

1. A container, comprising:
   a first chamber;
   a second chamber, wherein said second chamber surrounds said first chamber and is concentric with said first chamber, and wherein said first chamber is defined by an inner wall and said second chamber is defined by said inner wall and an outer wall, and wherein said inner wall protrudes above said second chamber, said container being under vacuum;
   a first means for selectively placing the first chamber in fluid flow communication with said second chamber;
   a second means for introducing material into the first chamber without releasing the vacuum of said second chamber;
   retaining means in the first chamber for retaining a solid component of a mixture of solids and liquid which is introduced into the first chamber; and
   means for selectively placing the interior of the container in communication with the atmosphere outside said container, whereby after introduction of a mixture of solids and liquid into said container, liquid passes through the retaining means and through said first means for selectively placing the first chamber in fluid flow communication with the second chamber, and into said second chamber with the solids being retained on said retaining means.

2. The container of claim 1 wherein said first means for selectively placing the first chamber in fluid flow communication with said second chamber comprises a lower stopper fitting within a bottom opening of said container, said stopper including a lower passage communicating with said first chamber, and a passage in said inner wall adjacent said second chamber, wherein said lower passage of said lower stopper is capable of being aligned with said passage of said inner wall adjacent said second chamber to provide for the flow of liquid from said first chamber to said second chamber.

3. The container of claim 2 wherein said retaining means includes a membrane disposed across said lower passage of said lower topper which communicates with said first chamber.

4. The container of claim 3 wherein said lower stopper includes a lower portion and an upper insert portion fitting within said lower portion and within said first chamber, said upper insert portion including said passage communicating with said first chamber; and said upper insert portion including said membrane disposed across said passage communicating with said first chamber.

5. The container of claim 1 wherein said means for selectively placing the interior of the container in communication with the atmosphere outside said container includes an upper stopper fitting within a top opening of said container, said upper stopper including an upper passage communicating with said first chamber; and an opening in said inner wall above said second chamber, wherein said upper passage of said upper stopper is capable of being aligned with said opening in said inner wall to provide for the passage of air from the outside atmosphere into said container.

6. The container of claim 5 wherein said upper stopper includes said second means for introducing material into the first chamber, without releasing the vacuum of said second chamber.

7. The container of claim 6 wherein said upper stopper includes an upper portion and a lower portion, said lower portion fitting within the top opening of said container, said lower portion including said upper passage communicating with said first chamber, and wherein said second means for introducing material into the first chamber without releasing the vacuum of the second chamber is a first self-sealing portion included in said upper portion of said stopper and a second self-sealing portion included in said lower portion of said upper stopper.

8. The container of claim 7 wherein said second self-sealing portion is a one-way valve fitting within said first chamber.

9. The container of claim 5, and further comprising a membrane disposed across said opening in said inner wall of said container, said membrane providing for the passage of air through said opening in said inner wall while preventing the passage of solid matter therethrough.

10. The container of claim 1 wherein said means for selectively placing the interior of the container in communication with the atmosphere outside said container includes an upper stopper fitting within a top opening of said container, said upper stopper including an upper portion and a lower portion, said lower portion fitting within the top opening of said container and said lower portion including a porous filter plug, and wherein said second means for introducing material into the first chamber without releasing the vacuum of the second chamber is a first self-sealing portion included in said upper portion of said stopper and a second self-sealing portion included in said lower portion of said upper stopper, and wherein said upper portion of said upper stopper is removable from said lower portion, whereby upon removal of said upper portion from said lower portion, air is enabled to pass through said filter plug and said second self-sealing portion into said first chamber.

* * * * *